(12) United States Patent
Shambaugh, Jr.

(10) Patent No.: US 7,942,805 B2
(45) Date of Patent: May 17, 2011

(54) VAD CONNECTOR PLUG

(75) Inventor: Charles R. Shambaugh, Jr., Coral Gables, FL (US)

(73) Assignee: Heartware, Inc., Miami Lakes, FL (US)

( * ) Notice: Subject to any disclaimer, the term of this patent is extended or adjusted under 35 U.S.C. 154(b) by 235 days.

(21) Appl. No.: 12/317,393

(22) Filed: Dec. 22, 2008

(65) Prior Publication Data

US 2009/0171136 A1 Jul. 2, 2009

Related U.S. Application Data

(60) Provisional application No. 61/009,412, filed on Dec. 27, 2007.

(51) Int. Cl.
*A61N 1/362* (2006.01)
(52) U.S. Cl. .......................................................... 600/16
(58) Field of Classification Search .................... 600/16; 604/175; 606/41; 623/1.15
See application file for complete search history.

(56) References Cited

U.S. PATENT DOCUMENTS

| | | | |
|---|---|---|---|
| 6,319,231 B1 * | 11/2001 | Andrulitis | 604/175 |
| 2004/0093075 A1 * | 5/2004 | Kuehne | 623/1.15 |
| 2004/0171905 A1 * | 9/2004 | Yu et al. | 600/16 |
| 2006/0276681 A1 * | 12/2006 | Bolling | 600/16 |

OTHER PUBLICATIONS

"A Felt Plug Simplifies Left Ventricular Assist Device Removal After Successful Bridge to Recovery" The Journal of Heart and Lung Transplantation, vol. 26, Issue 11, Nov. 2007, pp. 1209-1211.*
Cohn et al., "A Felt Plug Simplifies . . . ".*
Cohn et al., A Felt Plus Simplifies Left Ventricular Assist Device Removal After Successful Bridge to Recovery, The Journal of Heart and Lung Transplantation, Nov. 2007, vol. 26, pp. 1209-1211.
International Search Report issued by the International Bureau of WIPO in connection with International Application No. PCT/US08/13974.
Written Opinion of the International Searching Authority issued by the International Searching Authority (ISA/US) in connection with International Application No. PCT/US08/13974.
International Preliminary Report on Patentability issued by the International Bureau of WIPO on Jun. 29, 2010 in connection with International Application No. PCT/US2008/13974.
Written Opinion of the International Searching Authority issued by the International Searching Authority (ISA/US) in connection with International Application No. PCT/US2008/13974.

\* cited by examiner

*Primary Examiner* — George Manuel
*Assistant Examiner* — Robert N Wieland
(74) *Attorney, Agent, or Firm* — John P. White; Cooper & Dunham LLP

(57) ABSTRACT

A plug which may be positioned in place of a Ventricular Assist Device ("VAD") within a VAD connector mounted to the heart. The VAD connector may have at least one VAD-engaging feature and may define an opening. The plug may have a body adapted to fill the opening of the VAD connector and may engage the VAD connector. The plug may be installed in place of a VAD when the heart heals, and then removed and replaced by a VAD if the patient's condition deteriorates.

19 Claims, 5 Drawing Sheets

VAD CONNECTOR PLUG

The application claims benefit from U.S. Provisional Application No. 61/009,412, filed Dec. 27, 2007, the content of which is hereby incorporated herein by reference into this application.

BACKGROUND OF THE INVENTION

The present invention relates to components and methods used in connection with ventricular assist device connectors.

In certain disease states, the heart lacks sufficient pumping capacity to meet the needs of the body. This inadequacy can be alleviated by providing a mechanical pump referred to as a ventricular assist device ("VAD") to supplement the pumping action of the heart. Considerable effort has been devoted to providing a VAD which can be implanted and which can remain in operation for months or years to keep the patient alive while the heart heals, or which can remain in operation permanently during the patient's lifetime if the heart does not heal, or which can keep the patient alive until a suitable donor heart becomes available.

The VAD is typically connected to the heart, most commonly to the left ventricle. Typically, one end of a tube is connected to the VAD and the other end is connected to the aorta. Once connected, the VAD and the heart both pump blood from the left ventricle to the ascending or descending aorta to improve blood flow. Alternatively, a VAD may be connected to the ventricle to assist the heart in pumping blood into pulmonary arteries.

The VAD typically is connected to the heart through the use of a VAD connector, as disclosed in U.S. Published Patent Application Nos. 2004/0171905 and 2007/0134993, the disclosures of which are both hereby incorporated by reference herein. The VAD connector may be in the shape of a ring and is attached to the outer surface of the heart, commonly through the use of sutures. A separate surgical tool is then used to cut a hole in the ventricle centered within the VAD connector. A tube extending from the VAD is inserted through another hole in the left ventricle. The VAD is then attached to the VAD connector such that the tube of the VAD is positioned within the central opening of the VAD connector. The VAD connector is used to clamp the tube and thereby hold the VAD in position on the heart.

SUMMARY OF THE INVENTION

One aspect of the present invention provides a plug which can be positioned in place of a VAD within a VAD connector. The VAD connector typically is mounted to the heart and has at least one VAD-engaging feature and defines an opening. The plug may have a body adapted to fill the opening of the VAD connector and engage the VAD connector. Additionally, the plug may engage at least one VAD-engaging feature of the connector.

Another aspect of the present invention provides an assembly. The assembly may include a VAD connector mounted to the heart of a patient, having at least one VAD-engaging feature and defining an opening for communication between the interior of the heart and a VAD. The assembly desirably also includes a plug which fills the opening of the VAD connector and engages the VAD connector.

Yet another aspect of the present invention provides a kit. The kit according to this aspect of the invention desirably includes a VAD and a VAD connector mounted to the heart of a patient, the VAD connector desirably has at least one VAD-engaging feature and defines an opening. The VAD-engaging feature of the connector desirably is adapted to engage the VAD when the VAD connector is mounted on the heart of a patient. The kit also desirably includes a plug which may have a body adapted to fill the opening of the VAD connector and which further may engage at least one VAD-engaging feature of the VAD connector.

The functioning aspects of the invention incorporate the realization that in some situations, it would be desirable to remove the VAD but leave the VAD connector in place. For example, the heart may heal so that the VAD is no longer necessary. However, there may be a possibility that the patient's condition could lapse, thus reviving the need for the VAD. Also, the hole cut into the heart within the center of the VAD connector may not be repairable.

In still another aspect, the present invention may provide a method for treating heart disease of the type causing decreased blood pumping capacity. The method may include removing a VAD from an opening of a VAD connector mounted on the heart and inserting a plug into the opening of the VAD connector so that the plug blocks the opening while the VAD connector remains mounted on the heart. The method may further include the step of securing the plug to the VAD connector. In the event the condition of the heart deteriorates, thus requiring the reinstallation of the VAD, the method may further include the step of removing the plug from the VAD connector and engaging the VAD with the VAD connector.

DETAILED DESCRIPTION OF THE INVENTION

Figure 1A:
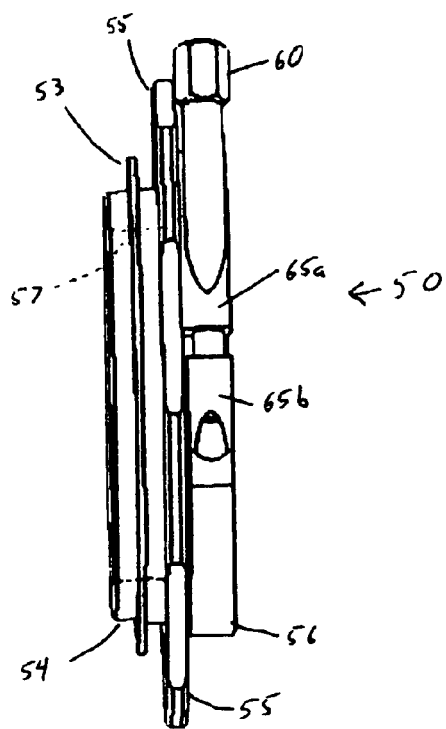
FIG. 1A is a side elevational view of a VAD connector utilized in one embodiment of the invention.
Figure 1B:
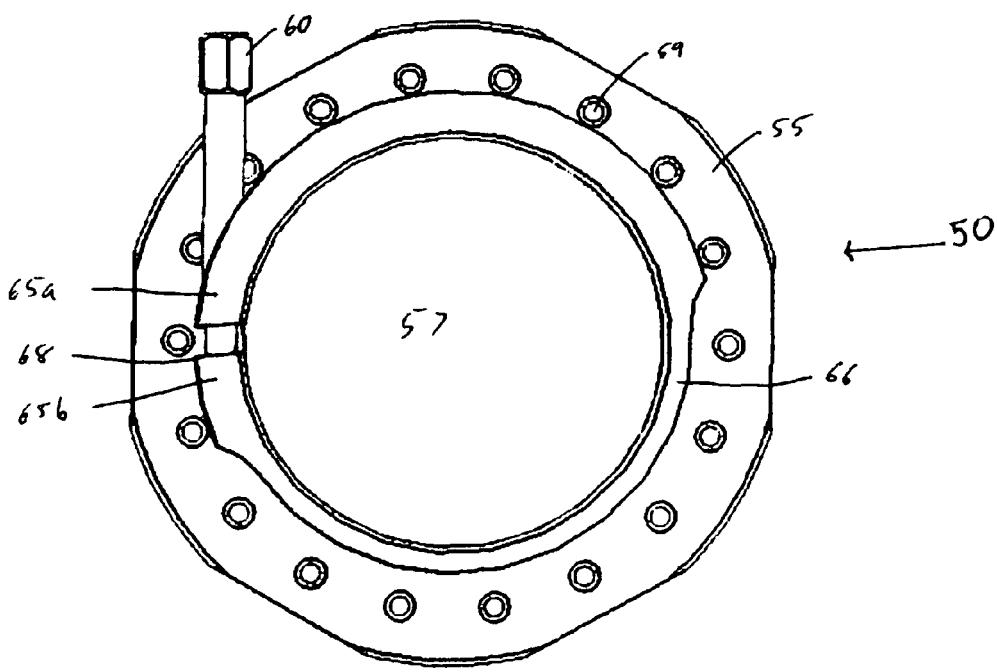
FIG. 1B is an end view of the VAD connector of FIG. 1A.

A kit according to one embodiment of the invention includes a VAD connector 50 shown in FIGS. 1A and 1B. The VAD connector 50 is generally ring-like. The VAD connector 50 includes a unitary metallic body having a flange 55, a first tubular projection 54 projecting in a first axial direction from the flange (to the left in FIG. 1A) from one side of flange 55. The unitary body also includes a second tubular projection 56 projecting from the opposite side of the flange in a second, opposite axial direction. The body defines with an interior bore 57 extending in the axial directions through the projections and flanges.

Figure 3:
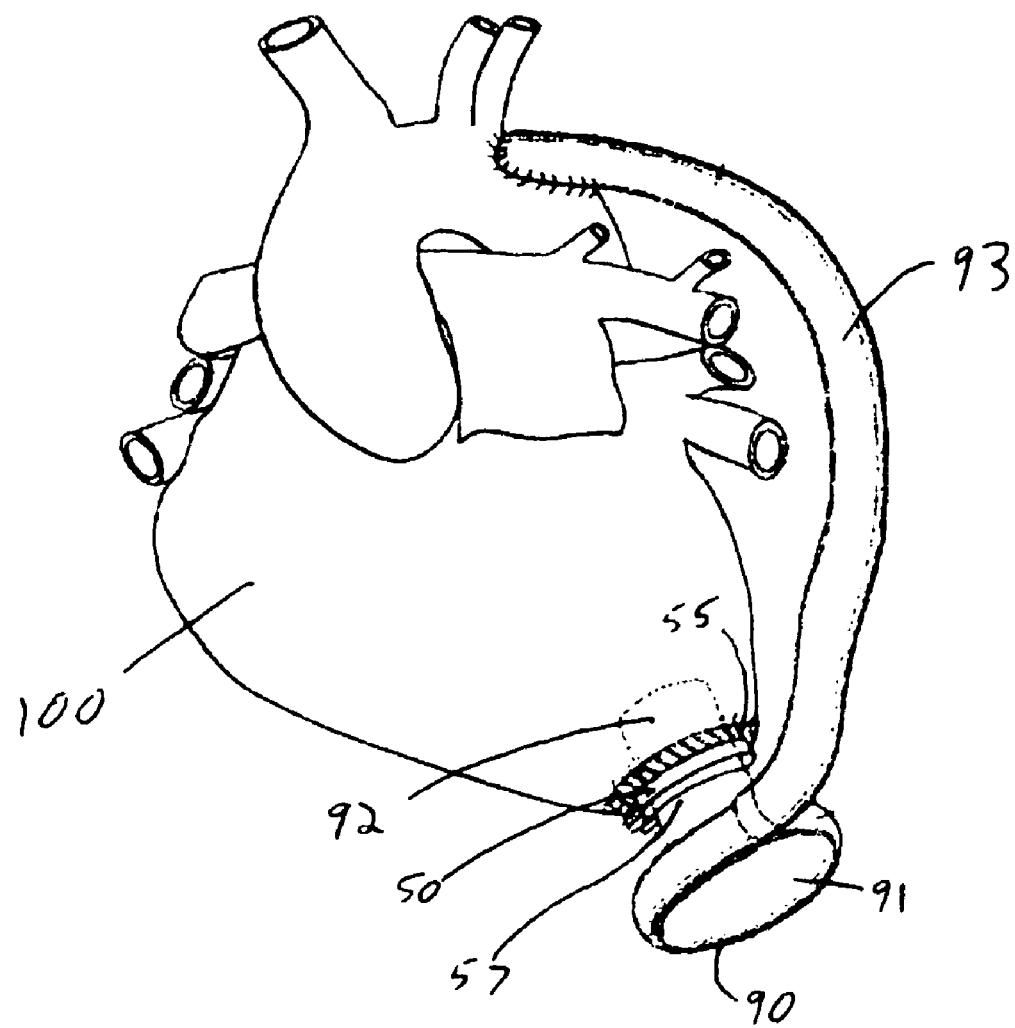
FIG. 3 is an illustration of a VAD and a VAD connector mounted onto the surface of the heart.

Flange 55 includes numerous perforations 59. As shown in FIG. 3, flange 55 can be used to secure the VAD connector 50 to the heart 100. For example, flange 55 may be attached to heart 100 using sutures or surgical staples. Moreover, flange 55 may allow for tissue in-growth. The outer surface 55 of flange 55 may be covered with a fabric material such as for example polyester material, expanded polytetrafluoroethylene, felt or any other such fabric well known in the art. The fabric covering may promote tissue in-growth to strengthen the attachment between the heart 100 and VAD connector 50.

The first tubular projection 54 has a substantially rigid wall extending around the entire periphery of opening 57. This wall is connected to flange 55 around the entire periphery of the opening. The first tubular projection has a lip 53 projecting outwardly from the exterior surface of the projection.

Figure 4A:
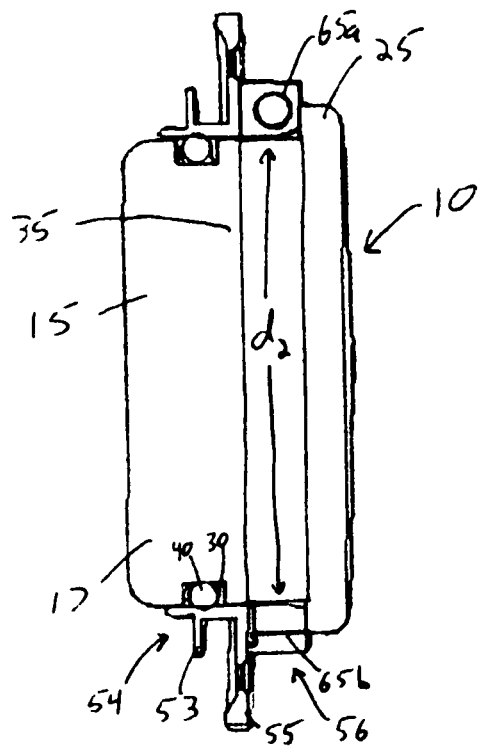
FIG. 4A is a cross-sectional view of one embodiment of a VAD connector and a plug inserted through the opening of the VAD connector.
Figure 4B:
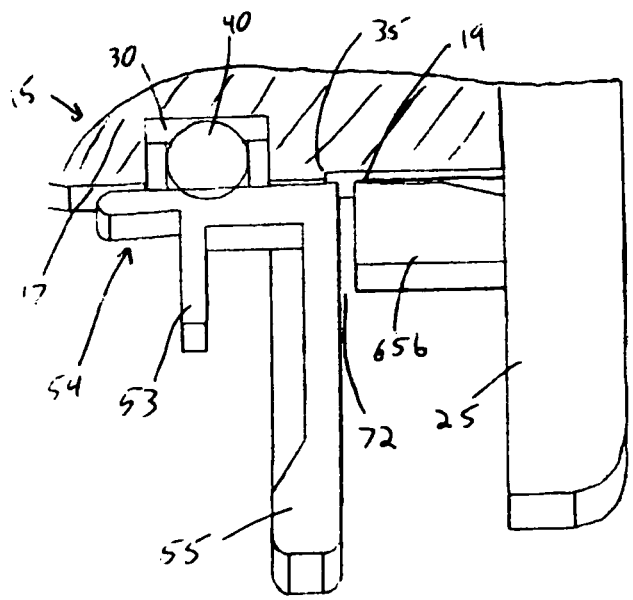
FIG. 4B is a cross-sectional view, as in FIG. 4A, zoomed in to show one embodiment of a VAD engaging feature of a VAD connector and plug.
Figure 5A:
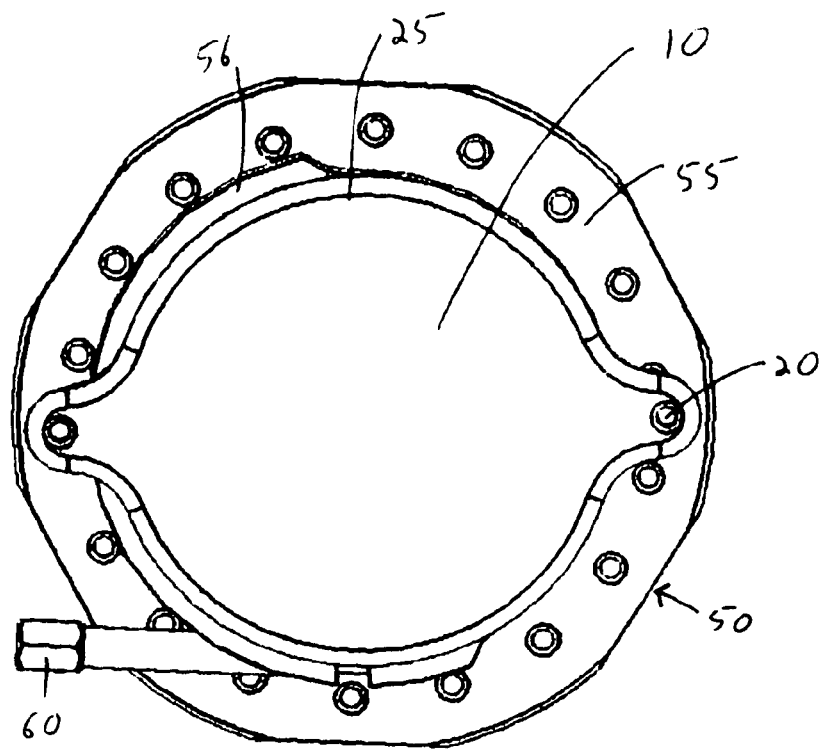
FIG. 5A is an end view of one embodiment of a VAD connector and a plug inserted through the opening of the VAD connector.
Figure 5B:
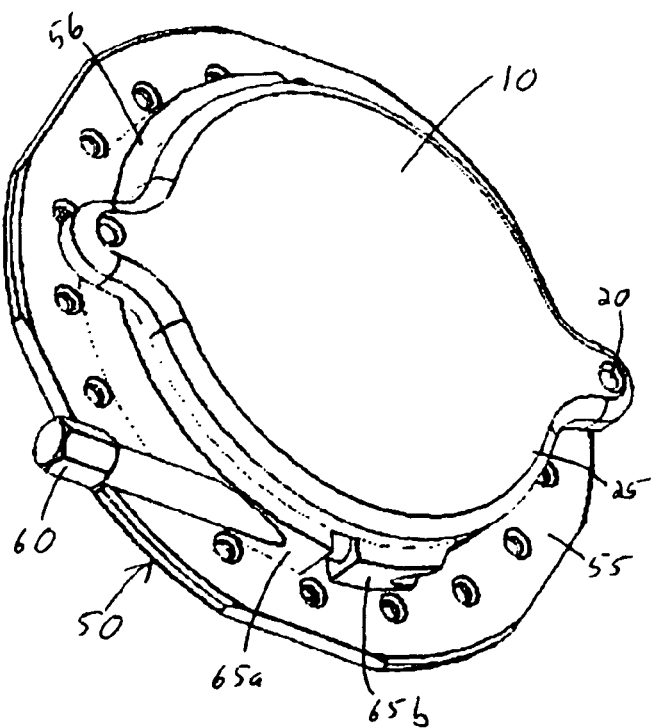
FIG. 5B is a perspective view of one embodiment of a VAD connector and a plug as shown in FIG. 5A.

The second tubular projection 56 includes a fixed wall portion 65A and a movable wall portion 65B. Fixed wall portion extends about approximately one-half the circumference of opening 57, whereas movable wall portion 65B extends around the other half of the circumference of the opening. Thus, the two portions 65A and 65B cooperatively define opening 57 within the second tubular projection 56. As best seen in FIG. 1B, the first wall portion 65A is relatively thick and rigid. The fixed wall portion is connected to flange 55 over the entire circumferential extent of the fixed wall portion. The second or movable wall portion 65B has a base end 66 integral with the fixed wall portion 65A and an opposite, free end 68 which is separate from the fixed wall portion. The movable wall portion 65B is not directly connected to the flange 55. As best seen in FIG. 4B, there is a gap 72 between the movable wall portion 65B and the flange. Thus, second or movable wall portion 65B is in the form of a curved cantilever arm, which is capable of flexing in the directions parallel to the plane of flange 55, toward or away from fixed wall portion 65A. The second or movable wall portion 65B has a relaxed position in which the movable portion 65B is further from the first or fixed wall portion 65A and a flexed position in which the movable wall portion is slightly closer to the fixed wall portion. When the second or movable wall portion 65B is in the relaxed position, the diameter of that portion of bore 57 within the second tubular projection 56 is equal to or slightly greater than the diameter of that portion of the bore 57 within the first tubular projection 54. When the second or movable portion 65B is in the flexed position, the diameter of that portion of the bore 57 within the second tubular projection 56, is slightly less than the diameter of the portion of bore 57 within the first tubular projection 54. Even when in the flexed position, the free end 68 of the movable wall portion typically does not contact the fixed wall portion 65A.

A screw 60 passes through the first or fixed wall portion 65A is secured thereto such that screw 60 cannot be removed from the fixed wall portion 65A. The screw 60 cannot be detached from the first portion 65A and fall into the patient during surgery. Screw 60 extends into the free end 68 of movable portion 65B. Screw 60 is threadedly engaged with the free end 68 of the second or movable wall portion. Screw 60 has a head that is engageable with a wrench, screwdriver or similar tool which may be used to rotate the screw. Rotation of screw 60 moves the second portion 65B between the relaxed and flexed positions. The wall portions 65A and 65B, together with screw 60, thus form a clamp which has first and second elements 65A and 65B disposed on opposite sides of opening 57 and movable relative to one another between an open position and a closed position. As the first and second portions 65A and 65B move towards the closed position, the distance between these elements decreases.

The VAD connector 50, and screw 60 may be as described in the aforementioned U.S. Published Patent Applications.

Figure 2A:
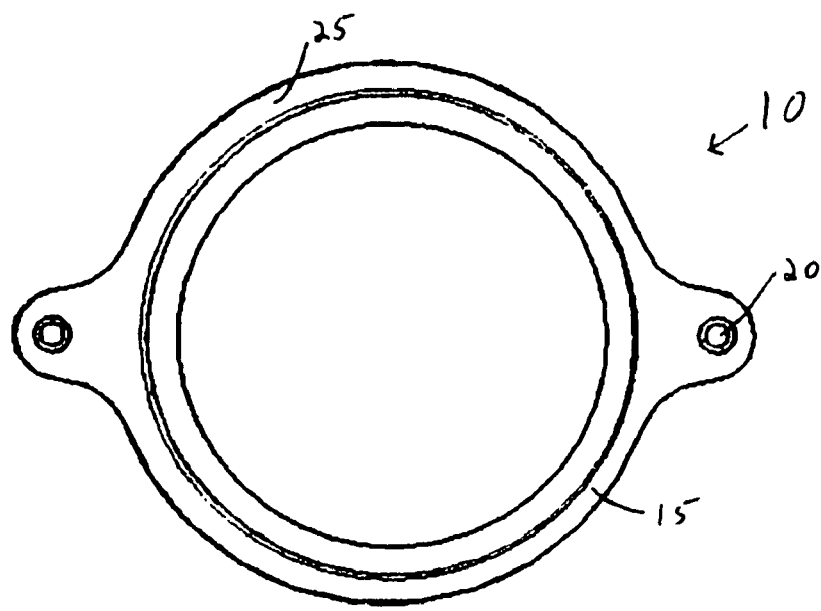
FIG. 2A is an end view of one embodiment of the plug of the present invention.
Figure 2B:
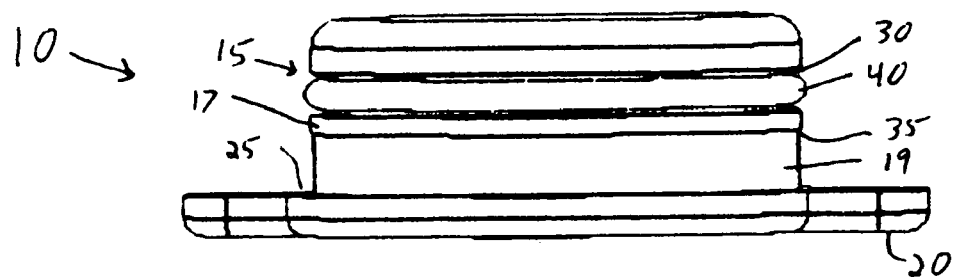
FIG. 2B is a side elevational view of the plug of FIG. 2A.

The kit according to this embodiment of the invention also includes a plug 10 illustrated in FIGS. 2A and 2B. Plug 10 includes a generally cylindrical body 15 and a shoulder 25 projecting radially outwardly from the body at one end. The body 15 has a main part 17 remote from shoulder 25 and a neck 19 extending between the main part and the shoulder. The diameter of the neck part 19 is slightly smaller than the diameter of the main part. A small ridge 35, best seen in FIG. 4B, is formed by the step in diameter at the juncture of neck 19 and main part 17. The surface of this ridge faces toward shoulder 25. The main part 17 of the body has a groove 30. A resilient O-ring 40 is positioned in groove 35. The plug 10 also has at least one suture connection in the form of one or more holes 20 extending through shoulder portion 25.

As illustrated in FIG. 3, the present invention may also include a VAD 90. VAD 90 includes a pump housing 91 and an intake element 92, which may be an integral part of the pump housing 91 of the VAD 90 or may be an intake tube connected to pump housing 91. The intake element 92 includes exterior features (not shown) similar to the features of the plug. Thus, the intake element of the VAD has an O-ring (not shown) similar to the O-ring 40 of the plug, and also has a shoulder similar to shoulder 35 of the plug. The VAD has an outlet tube 93 connected to the pump housing, and also includes internal structures adapted to pump blood as, for example, a pump rotor and drive for spinning the rotor. For example, the internal structure of the VAD may be as shown in U.S. Pat. Nos. 6,368,083; 6,688,861; and 7,027875.

In a method according to an embodiment of the invention, VAD connector 50 is attached to the heart 100 of a patient. The VAD connector 50 may be attached to the outer surface of the heart 100 by means such as sutures, surgical adhesives, surgical staples, or the like to secure flange 55 the wall of the heart 100. Flange 55 may have a covering which allows for tissue in-growth, creating an even stronger bond between the heart 100 and VAD connector 50. The VAD connector is placed at the desired location of the VAD as, for example, at or near the apex of the left ventricle if the VAD is to assist the pumping action of the left ventricle, or in a corresponding location on the right ventricle for right ventricular assistance.

A hole is cut through the wall of the ventricle. Connector 50 is positioned so that the first tubular projection 54 of connector 50 extends into the hole, and so that bore 57 of the connector communicates with the interior of the heart through the hole.

Lip 53 passes through the hole in the heart 100 and abuts the inner surface of the wall of the heart 100, so that the lip further secures connector 50 to the heart.

When the VAD 90 is mounted in the VAD connector 50, as illustrated in FIG. 3, the intake element 92 of the VAD 90 extends into the bore 57 of the VAD connector 50 and communicates with the interior of the ventricle through the opening 57. The intake element 92 of VAD 90 is secured within the opening 57 of VAD connector 50 such that a secure, leak-proof seal is ensured. The intake element of the VAD is secured to the VAD and sealed to the VAD in the same manner as discussed below with reference to the plug 10. The VAD outlet tube 93 is connected to an appropriate artery, typically the aorta for left ventricular assist.

After implantation of the VAD, the patient may recover to the point where continued use of the VAD is believed unnecessary. At this time, the VAD may be removed from the patient by disconnecting the VAD from the VAD connector and inserting the plug 10 in place of the VAD. As illustrated in FIGS. 4A-B and 5A-B, plug 10 may be positioned within the VAD connector 50 in place of VAD 90.

When the plug 10 is inserted in the VAD connector 50, the body 15 of the plug fills the opening 57 of VAD connector. Shoulder portion 25 of the body rests on the outer end the second tubular projection, i.e., on the end of the second tubular projection remote from flange 55. Engagement of shoulder limits the distance plug 10 can be inserted into VAD connector 50. When the plug 10 is positioned in VAD connector 50, the main part 17 of the plug body is disposed within the first tubular projection 54 of the connector, so that the O-ring 30 of the plug bears on the rigid wall of projection 54. The O-ring and plug thus seal bore 57 of the VAD connector.

During removal of the VAD, screw 60 is loosened so as to bring the second or movable wall portion 65B to its relaxed position, and thus open the clamp formed by wall portions 65A and 65B of the second tubular projection 56. Once the plug 10 is seated in the VAD connector, the physician tightens screw 60 to move the second or movable wall portion to its flexed position, thereby closing the clamp. When the clamp is fully closed, the internal diameter $d_2$ bore 57 within second projection 56 (FIG. 4A), at one or more points around the circumference of the bore, is less than the diameter of plug main portion 15. Thus, the portions 65A and 65B of the second projection form a positive mechanical lock which will retain the plug 10 in the VAD connector. Retraction of the plug out of the connector will be blocked by engagement of the ledge 35 on the plug (FIG. 4B) with one or both portions 65A and 65B of the second projection 56. Preferably, the portions 65A and 65B bear on the neck 19 of the plug, and frictionally engage the neck. As a result, the plug 10 is locked in place within the VAD connector. As mentioned above, the intake element 92 of the VAD has features including a ledge and O-ring similar to those of the plug. When the VAD is installed in the connector 50, the same features of the connector which mechanically retain the plug and form a seal with the plug serve to mechanically retain the VAD and form a seal with the VAD. These features include the clamp formed by the first and second portions 65A and 65B and the interior surface of the first tubular projection 54. Because these features engage the VAD when the VAD is installed, they are referred to herein as "VAD-engaging" features of the connector. Because the VAD-engaging features of the connector are also used to engage plug 10 when the plug is installed, there is no need to provide additional features on the connector to engage the plug. This simplifies the construction of the connector. The plug 10 may be additionally secured in place by suturing the plug to the flange of the connector or to the heart, using sutures extending through the suture holes 20 of the plug.

When the plug 10 is installed in the VAD connector 50, the plug and connector form an assembly which remains in place on the patient's heart and closes the opening in the heart wall. This assembly may remain in place for a prolonged period, and in some cases for the entire lifetime of the patient.

Leaving the assembly in place avoids certain problems which can arise upon removal of the VAD connector from the heart. For example, removing the sutures or staples which hold the connector from the outer surface of the heart could cause additional injury to the wall of the heart. Also, the hole in the wall of the heart 100, cut during attachment of VAD connector 50 or implantation of VAD 90, may not heal properly if the VAD connector 50 is removed.

Moreover, there is the possibility that the heart 100, once healed, could relapse into its previous ailing condition. If the patient's condition deteriorates so that ventricular assist is needed again, the plug may be removed by opening the clamp formed by wall portions 65A and 65B of the second projection 56 and pulling the plug out of the connector. VAD 90 may be reinstalled by inserting the intake element into the connector and closing the clamp. There is no need to cut a new opening in the heart wall or install another connector, and thus there is little or no trauma to the heart. The VAD 90 which is reinstalled may be the same VAD as originally installed or a new VAD having an intake element with the same configuration.

In a method according to a further embodiment of the invention, the VAD connector 50 may be installed on the heart 100 and the plug 10 may be inserted into the VAD connector without first installing a VAD in the connector. This leaves the same assembly of the connector 50 and plug 10 in place on the heart, so that the patient is ready for VAD installation at a later time. A kit for performing this method may include only the plug and the connector, without the VAD. This method may be a preemptive method in which the VAD connector 50 is attached to the heart 100, while heart 100 is reasonably healthy and not, as of yet, in need of a VAD 90. Typically, this would be done if the physician anticipates that the patient will need a VAD in the future. In the event the condition of heart 100 deteriorates, and a VAD 90 is needed, the plug 10 may be removed from VAD connector 50 and a VAD 90 may be inserted.

This embodiment may allow the initial trauma caused by installing the VAD connector 50 and cutting an opening therethrough to heal at a time when the condition of heart 100 has not yet deteriorated to the point that a VAD 90 is required. Then, if a VAD 90 is required later, for example, in a situation where the condition of heart 100 deteriorates, a VAD 90 may be inserted into heart 100 with a much smaller amount of trauma occurring when the VAN is inserted into the heart. This approach may be beneficial because, when the trauma to the heart associated with installation of the connector occurs while the heart 100 is still reasonably healthy, the patient may have a better chance of surviving.

The particular VAD-engaging features of connector 50, and the corresponding features of plug 10 and VAD 90 discussed above are merely illustrative. For example, the clamp and ledge arrangement discussed above may be replaced by a threaded connection, bayonet lock or other arrangement for securing the VAD or plug to the connector. Likewise, the O-ring seal may be replaced by a tapered element on the connector, such as a tapered bore within the connector, and a matching tapered element on the VAD which fits together with the tapered element of the connector. In these arrangements as well, the plug may be provided with features corresponding to the features of the plug and arranged to interact with the VAD-engaging features of the connector.

In still other embodiments, the plug 10 may have other engagement features to provide mechanical attachment between plug 10 and VAD connector 50 using features of the connector different from those used to secure the VAD to the connector. Merely by way of example, where the VAD is held in place by a clamp arrangement as discussed above, the plug may be held to the connector by small screws passing through the shoulder of the plug and engaging threaded holes in the flange of the connector. Also, the plug may seal to a different portion of the connector than the VAD. These different features can be used in addition to, or in lieu of, engagement between the plug and the VAD-engaging features.

Plug 10, the first and second tubular projections 54 and 56 of VAD connector 50, the housing 91 of VAD 90 and screw 60 are preferably made of titanium. However, any suitable metal, metals, combination of metals or any other suitable material or materials such as polymers or ceramics, for example, may be used to manufacture or make the above components so long as the material is bio-compatible and non-thrombogenic. Other materials may be used which may be thrombogenic, so long as a bio-compatible, non-thrombogenic coating is applied to the surface of the material.

The plug 10 desirably has very smooth surfaces to inhibit cellular attachment to the plug. Plug 10 may further include a coating which may inhibit cell growth or attachment thereon. Any type of coating known in the art may be used to coat plug 10. These features help to assure the plug 10 does not become permanently attached to the VAD connector or the heart due to tissue growth while the plug is in place.

As these and other variations and combinations of the features discussed above can be utilized, the foregoing description of the preferred embodiments should be taken by way of illustration rather than by way of limitation of the invention as defined by the claims.

What is claimed is:

1. A plug to be positioned, during a surgical procedure, in place of a VAD within a VAD connector mounted to the heart and having at least one VAD-engaging feature and defining an opening, the plug comprising a body comprising metallic, ceramic or polymeric material, adapted to fill the opening of the VAD connector, engage the VAD connector and remain in place within the VAD connector following the surgical procedure.

2. A plug as claimed in claim 1 wherein the plug is adapted to engage the at least one VAD-engaging feature of the connector.

3. A plug as claimed in claim 2 wherein the plug body is adapted for engagement by a clamp on the connector.

4. A plug as claimed in claim 2 wherein the plug engages the at least one VAD-engaging feature of the connector with a groove and an O-ring.

5. A plug as claimed in claim 1 wherein the material of the plug body is non-thrombogenic.

6. A plug as claimed in claim 5 wherein the non-thrombogenic material is titanium.

7. A plug as claimed in claim 1 wherein the plug body has a surface which inhibits cell growth or attachment.

8. An assembly including:
   a VAD connector mounted to the heart of a patient, the VAD connector having at least one VAD-engaging feature including a clamp having first and second elements disposed on opposite sides of the opening, the clamp having an open condition in which the first and second elements are further from one another and a closed condition in which the first and second elements are closer to one another and defining an opening for communication between the interior of the heart and a VAD; and
   a plug filling the opening of the VAD connector and engaged with the connector, wherein the plug has a body having a main portion and a neck with smaller diameter than the main portion, a distance between the elements of the clamp being less than the diameter of the main portion when the clamp is in the closed condition.

9. An assembly as claimed in claim 8 wherein the plug engages the at least one VAD-engaging feature of the connector.

10. A kit for the surgical treatment of heart disease, comprising:
    a VAD connector adapted to be mounted to the heart of a patient, the VAD connector having at least one VAD-engaging feature adapted to engage a VAD, the VAD connector defining an opening; and
    a plug having a metallic, ceramic or polymeric body, adapted to fill the opening of the connector, engage the connector and remain in place within the connector following the surgical treatment.

11. A kit as claimed in claim 10 further comprising a VAD adapted for engagement with the at least one VAD-engaging feature of the connector.

12. A kit as claimed in claim 10 wherein the plug is adapted to engage the at least one VAD-engaging feature of the connector.

13. A kit as claimed in claim 10 wherein the VAD-engaging features of the connector include a clamp having first and second elements disposed on opposite sides of the opening, the clamp having an open condition in which the first and second elements are further from one another and a closed condition in with the first and second elements are closer to one another, the plug body having a main portion and a neck with smaller diameter than the main portion, a distance between the elements of the clamp being less than the diameter of the main portion when the clamp is in the closed condition.

14. The kit as claimed in claim 10, wherein the plug body comprises titanium.

15. A method of treating heart disease, comprising: removing a VAD from an opening of a VAD connector mounted on the heart; and
    inserting a plug into the opening of the VAD connector so that the plug blocks the opening while the VAD connector remains mounted on the heart, and securing the plug to the VAD connector.

16. A method as claimed in claim 15 wherein the step of securing the plug to the VAD connector includes engaging the plug with an at least one VAD-engaging feature of the VAD connector.

17. A method as claimed in claim 15 further comprising the step of removing the plug from the VAD connector and engaging a VAD with the VAD connector.

18. A method of performing a surgical procedure for preemptively treating heart disease of the type causing decreased blood pumping capacity, comprising:
    attaching a VAD connector to the outer surface of the heart, the VAD connector defining an opening communicating with the interior of a ventricle; and
    inserting a plug comprising a metallic, ceramic or polymeric body into the opening of the VAD connector so that the plug blocks the opening, wherein the plug is adapted to remain in place within the VAD connector following the surgical procedure.

19. The method as claimed in claim 18, further comprising the steps of removing the plug from the opening of the VAD connector and inserting a VAD.

* * * * *